US005533999A

United States Patent [19]
Hood et al.

[11] Patent Number: 5,533,999
[45] Date of Patent: Jul. 9, 1996

[54] METHOD AND APPARATUS FOR MODIFICATIONS OF VISUAL ACUITY BY THERMAL MEANS

[75] Inventors: Larry Hood, Laguna Hills, Calif.;
Antonio Mendez G., Mexicali, Mexico

[73] Assignee: Refractec, Inc., Laguna Niguel, Calif.

[21] Appl. No.: 523,591

[22] Filed: Sep. 5, 1995

Related U.S. Application Data

[63] Continuation of Ser. No. 111,296, Aug. 23, 1993.

[51] Int. Cl.$^6$ .................................................. A61B 17/36
[52] U.S. Cl. .................................................. 606/5
[58] Field of Search ................................ 606/4, 5, 6, 27, 606/28, 29, 32, 35, 40, 41, 48, 51, 52

[56] References Cited

U.S. PATENT DOCUMENTS

| | | |
|---|---|---|
| 3,776,230 | 12/1973 | Neefe . |
| 4,326,529 | 4/1982 | Doss et al. . |
| 4,381,007 | 4/1983 | Doss . |
| 4,461,294 | 7/1984 | Baron . |
| 4,633,870 | 1/1987 | Sauer ........................................ 606/8 |
| 4,729,372 | 3/1988 | L'Esperance, Jr. . |
| 4,747,820 | 5/1988 | Hornlein et al. . |
| 4,798,204 | 1/1989 | L'Esperance, Jr. . |
| 4,907,585 | 3/1990 | Schachar ................................. 606/28 |
| 4,931,047 | 6/1990 | Broadwin et al. . |
| 4,976,709 | 12/1990 | Sand . |
| 4,988,334 | 1/1991 | Hornlein et al. . |
| 5,015,227 | 5/1991 | Broadwin et al. . |
| 5,025,811 | 6/1991 | Dobrogowski et al. . |
| 5,035,695 | 7/1991 | Weber, Jr. et al. . |
| 5,071,418 | 12/1991 | Rosenbaum . |
| 5,137,530 | 8/1992 | Sand . |
| 5,217,459 | 6/1993 | Kamerling ................................. 606/4 |
| 5,312,401 | 5/1994 | Newton et al. . |
| 5,346,491 | 9/1994 | Oertti ...................................... 606/37 |

FOREIGN PATENT DOCUMENTS

WO90/12618  11/1990  WIPO .

OTHER PUBLICATIONS

"An Electrothermal Technique for the alteration of Corneal Curvature," Doss, et al., Los Alamos Scientific Lab, Feb., 1978.

"A Technique for the Selective Heating of Corneal Stroma," Doss, et al., Contact & Intraocular Lens Medical Jrl., vol. 6, No. 1, Jan.–Mar., 1980, pp. 13–17.

"Bipokeratoplasty: using cautery to advantage," Fugo, Ocular Surgery News, Feb., 1993, pp. 101 & 113.

"Combined Microwave Heating and Surface Cooling of the Cornea," Trembly, et al., IEEE Transactions On Biomedical Engineering, vol. 38, No. 1, Jan., 1991, pp. 85–91.

"Regression of Effect Following Radial Thermokeratoplasty in Humans," Feldman, et al., Refractive and Corneal Surgery, vol. 5, Sep./Oct., 1989, pp. 288–291.

"The Need For Prompt Prospective Investigation," McDonnell, Refractive & Corneal Surgery, vol. 5, Jan./Feb., 1989.

*Primary Examiner*—Angela D. Sykes
*Assistant Examiner*—Sonya Harris-Ogugua
*Attorney, Agent, or Firm*—Blakely, Sokoloff, Taylor & Zafman

[57] ABSTRACT

A thermokeratoplastic electrode which has a tip that is placed in direct contact with the epithelium layer of the cornea. The electrode is capable of creating very small localized denatured areas that shrink the corneal membrane to correct hyperopic and astigmatic conditions.

5 Claims, 3 Drawing Sheets

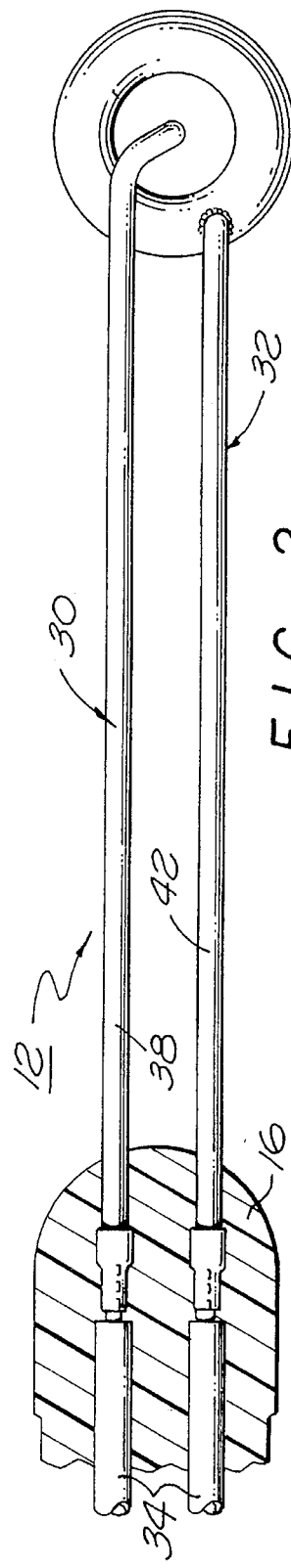
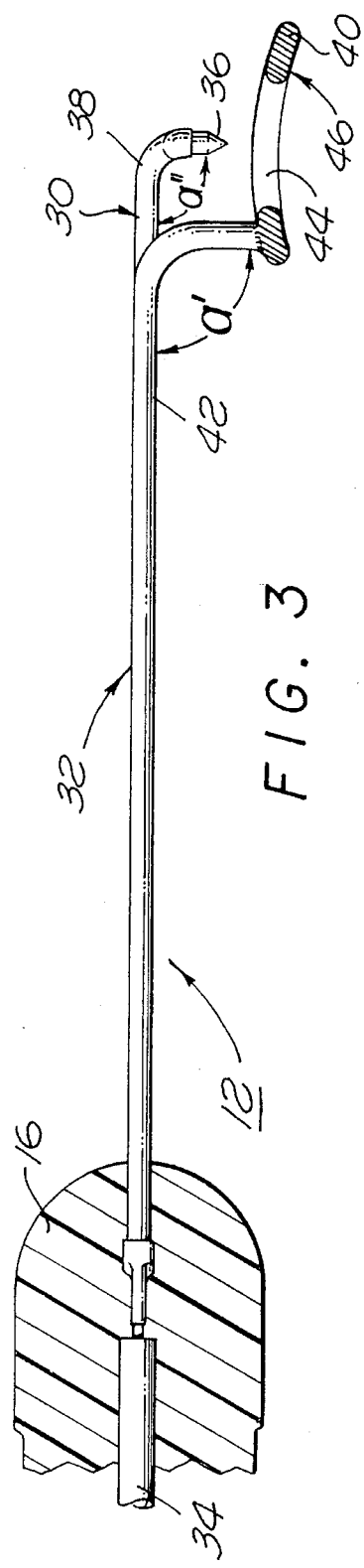
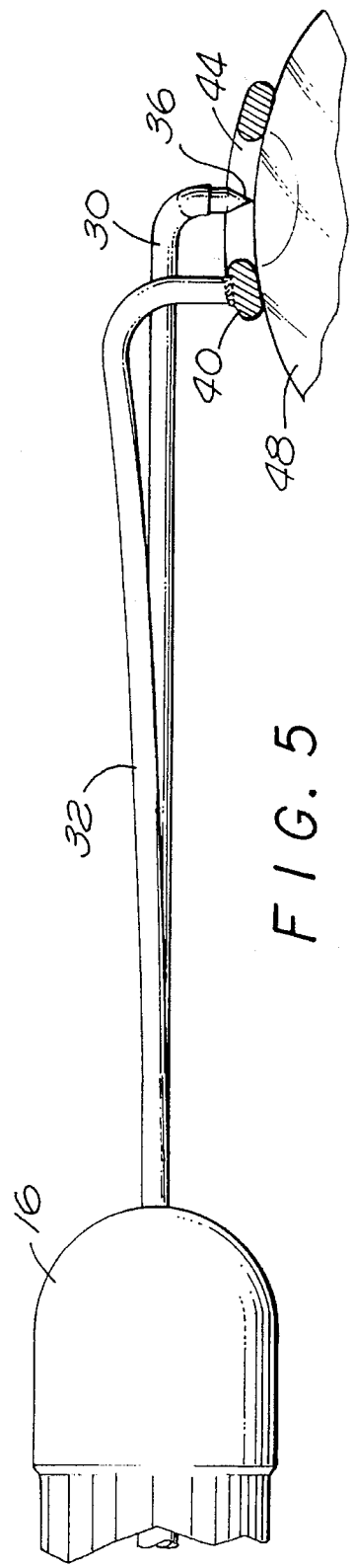

METHOD AND APPARATUS FOR MODIFICATIONS OF VISUAL ACUITY BY THERMAL MEANS

This is a continuation of application Ser. No. 08/111,296 filed Aug. 23, 1993.

BACKGROUND OF THE INVENTION

1. Field of the Invention

The present invention relates to a thermokeratoplastic probe that is placed into direct contact with the outer surface of the cornea.

2. Description of Related Art

Techniques for correcting vision have included reshaping the cornea of the eye. For example, myopic conditions can be corrected by cutting a number of small incisions in the corneal membrane. The incisions allow the corneal membrane to relax and increase the radius of the cornea. The incisions are typically created with either a laser or a precision knife. The procedure for creating incisions to correct myopic defects is commonly referred to as radial kerectotomy and is well known in the art.

The techniques of radial kerectotomy are only effective in correcting myopia. Radial kerectotomy cannot be used to correct a eye condition such as hyperopia. Additionally, kerectotomy has limited use in reducing or correcting an astigmatism. The cornea of a patient with hyperopia is relatively flat. A flat cornea creates a lens system which does not direct the focal point of the viewed image to the optic nerve of the eye. Hyperopia can be corrected by reshaping the eye to decrease the radius of cornea. It has been found that hyperopia can be corrected by heating and denaturing local regions of the corneal membrane layer. The denatured tissue contracts the cornea and changes the shape of the eye. The procedure of heating the corneal membrane to correct a patient's vision is commonly referred to as thermokeratoplasty.

U.S. Pat. Nos. 4,461,294 issued to Baron; 4,976,709 issued to Sand and PCT Publication WO 90/12618, all disclose thermokeratoplastic techniques which utilize a laser to heat the corneal membrane. Although effective in reshaping the eye, the laser based systems of the Baron, Sand and PCT references are relatively expensive to produce. Expensive laser systems increase the cost of the procedure and are economically impractical for doctors with limited financial resources.

U.S. Pat. Nos. 4,326,529 and 4,381,007 issued to Doss disclose electrodes that are used to heat the corneal membrane of an eye. The electrode is located within a housing that spaces the tip of the electrode from the surface of the eye. An isotropic saline solution is irrigated through the electrode and aspirated through a channel formed between the outer surface of the electrode and the inner surface of the sleeve. The saline solution provides an electrically conductive medium between the electrode and the corneal membrane. The current from the electrode heats the outer layers of the eye. Subsequent cooling of the heated outer eye tissue causes the cornea to shrink to a new radial shape. The saline solution also functions as a coolant which cools the outer epithelium layer, so that the corneal membrane has a more uniform temperature gradient across the thickness of the eye.

The saline solution of the Doss device spreads the current of the electrode over a relatively large area of the cornea. Consequently, thermokeratoplasty techniques using the Doss device are limited to reshaped corneas with relatively large denatured areas. It is desirable to provide an electrode which can locally heat very small areas of the cornea. An electrode that creates relatively small heated areas would allow more flexibility in reshaping the cornea. This is particularly true if thermokeratoplasty is used to correct astigmatic conditions. It would therefore be desirable to have a thermokeratoplastic electrode which will allow the surgeon to heat relatively small areas of a corneal membrane.

SUMMARY OF THE INVENTION

The present invention is a probe which has an electrode that is placed in direct contact with the epithelium layer of the cornea and is used to locally heat the corneal membrane. The probe includes a first electrode that has a tip which extends from a cantilevered beam. Spaced from the tip is a disk which extends from a second cantilevered beam. The disk and second beam define a second electrode that provides a return path for the first electrode. The tip is concentric with an aperture located within the disk.

To heat a portion of the eye, the disk is placed onto the eye and depressed until the tip extends through the aperture and comes into contact with the epithelium layer of the cornea. Power is supplied to the electrode to create of flow of current from the first electrode, through the eye and back into the second electrode. The radius of the tip and the power supplied to the electrode are such that a denatured area as small as 1 millimeter can be formed by the probe. A pattern of denatured areas can be created in the corneal membrane to correct hyperopic or astigmatic conditions. Additionally, the small denatures areas can also be utilized to correct radial keratotomy procedures that overcorrect for myopia.

It is therefore an object of the present invention to provide a thermokeratoplastic electrode that creates relatively small denatured areas in a corneal membrane.

It is also an object of the present invention to provide an inexpensive and effective thermokeratoplasty procedure.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 2 is a top view of an electrode probe of the system;

FIG. 3 is a side view of the probe in FIG. 2;

FIG. 5 is a side view showing the probe being used to denature an area of the corneal membrane;

DETAILED DESCRIPTION OF THE INVENTION

Figure 1:
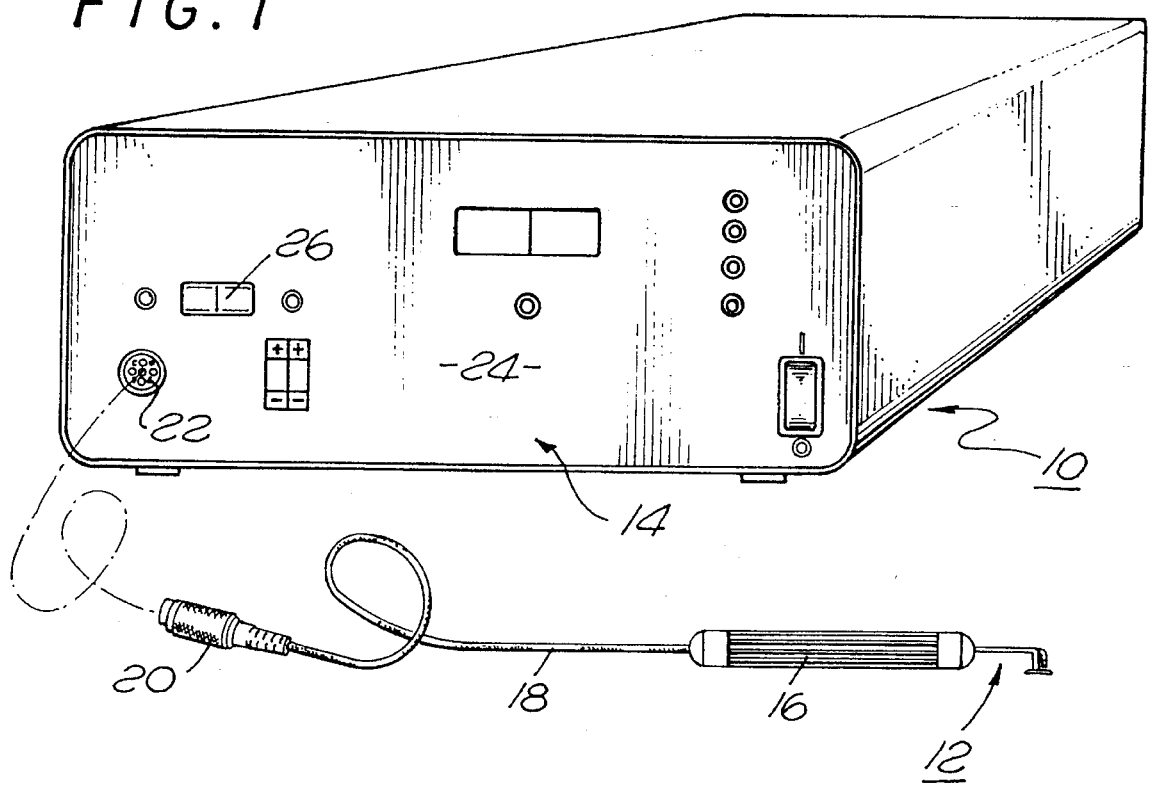
FIG. 1 is a perspective view of a thermokeratoplastic electrode system of the present invention.

Referring to the drawings more particularly by reference numbers, FIG. 1 shows a thermokeratoplastic electrode system 10 of the present invention. The system 10 includes an electrode probe 12 coupled to a power supply unit 14. The power supply unit 14 contains a power supply which can deliver power to the probe 12. The probe 12 has a hand piece 16 and wires 18 that couple the probe electrodes to a connector 20 that plugs into a mating receptacle 22 located on the front panel 24 of the power unit. The hand piece 16 is typically constructed from a dielectric plastic material and is approximately 0.5 inches in diameter and 5 inches long. In the preferred embodiment, the power supply provides a constant current source. To protect the patient from overvoltage, the power unit 14 may have an upper voltage limit which terminates power to the probe when the output voltage of the unit exceeds a predetermined value. The power unit 14 may also contain monitor and alarm circuits which monitor the resistance or impedance of the load and provide an alarm when the resistance/impedance value exceeds and/or falls below predefined limits. The alarm may provide either an audio and/or visual indication to the user that the resistance/impedance value has exceeded the outer predefined limits. Additionally, the unit may contain a ground fault indicator. The front panel of the power unit typically contains meters and displays that provide an indication of the power, frequency, etc., of the power delivered to the probe.

The power unit 14 preferably delivers a highly damped power output in a frequency range of 50 KHz–1 MHz, with a nominal frequency of 300 KHz. The output voltage is typically 150 V supplied to a load of approximately 200 ohms ($\Omega$). The system has a foot switch (not shown) which controls the application of power to the probe 12. The power unit 14 also contains a timer circuit which allows power to be supplied to the probe 12 for a predetermined time interval. The timer may be a Dose timer or other similar conventional circuitry which terminates power to the probe after a predetermined time interval. The power unit 14 may have a control member 26 to allow the user to select between a unipolar or a bi-polar operation. The front panel of the power unit may also have control members (not shown) that allow the surgeon to vary the power, frequency, timer interval, etc. of the unit. The ground pad (not shown) for a unipolar probe may be coupled to the power unit through a connector located on the back panel of the unit. To operate the system, the surgeon depresses the foot switch and a short surge of power is supplied to the probe 12. The power unit may be a device manufactured by Rose Electrotherapy located in Los Angeles, Calif., which sells the unit as model 1400, serial number 1836. The power utilized in the present invention typically correlates to a 20% power setting on the Rose device. The time interval is typically set between 0.2–3.0 seconds, preferably at 1.0 seconds.

Figure 4:
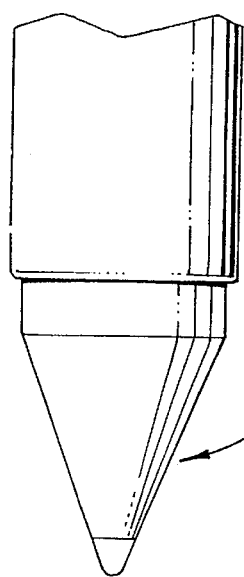
FIG. 4 is an enlarged view of the probe tip.

FIGS. 2–4, show a preferred embodiment of the probe 12. The probe 12 has a first electrode 30 and a second electrode 32. Although two electrodes are described and shown, it is to be understood that the probe may have either both electrodes (bipolar) or just the first electrode (unipolar). If a unipolar probe is used, a "ground pad" (indifferent electrode) is typically attached to the patients back to provide a "return" path for the current of the electrode.

Both electrodes 30 and 32 extend from the hand piece 16 which contains a pair of internal wires 34 that are crimped or soldered to the end of the electrodes. The first electrode 30 has a tip 36 which extends from a first spring member 38 that is cantilevered from the hand piece 16. The electrode 30 is preferably constructed from a phosphor, bronze or stainless steel wire that is 1.0 mm in diameter. The spring portion 38 of the first electrode 30 is preferably 50 millimeters (mm) long. In the preferred embodiment, the tip 36 has an included angle of between 15°–60°, 30° nominal, and a nose radius of approximately 50 microns. A majority of the electrode 30 is covered with an insulating material to prevent arcing, and to protect the user.

The second electrode 32 includes a disk portion 40 which extends from a second spring member 42 that is also cantilevered from the hand piece 16. The disk portion 40 is spaced a predetermined distance from first electrode 30 and has an aperture 44 that is concentric with the tip 36. In the preferred embodiment, the disk portion 40 has an outer diameter of 5.5 mm and an aperture diameter of 3.0 mm. The disk 40 further has a concave bottom surface 46 that generally conforms to the radius of a cornea. In the preferred embodiment, the bottom surface 46 has a spherical radius of approximately 12.75 mm. The second electrode 32 provides a return path for the current from the first electrode 30. To insure proper grounding of the cornea, the surface area of the disk 40 is typically 20–500 times larger than the contact area of the tip 36. In the preferred embodiment, the second spring member 42 is constructed to have a spring constant that is no greater than one-half the stiffness of the first spring member 38, so that the second electrode 32 will have a greater deflection per unit force than the first electrode 30. As shown in FIG. 3, the tip 36 and disk 40 are typically located at angles a' and a" which may range between 30°–180°, with the preferred embodiment being 45°.

FIG. 5 shows the operation of the probe 12. A peribulbar anesthesia is first administered to the patient and the eye 48 is stabilized. As an alternative to the peribulbar anesthesia, the surgeon may use a topical anesthesia such as proparacaine drops. The cornea of the eye is then marked at a location which is to be denatured. The probe 12 is placed onto the eye 48 so that the disk 40 is adjacent to the cornea. A gentle force is applied to the probe 12 to deflect the second electrode 32, until the tip 36 of the first electrode 30 is in contact with the cornea 48. The surgeon may apply a force sufficient to slightly depress the cornea with the tip 36 of the first electrode 30, to insure that there is a direct electrical path between the electrode 30 and the eye. The surgeon then depresses the foot switch so that the power unit 14 delivers a current to the first electrode 30. The current flows through the outer layers of the corneal membrane and back into the second electrode 32. The time interval of the energy surge may be set to create a denatured area approximately 1.0 mm in diameter. The eye is allowed to cool, wherein the denatured area contracts the corneal membrane. The surgeon then tests the eye to determine if the vision deficiency has been corrected. If correction has not been achieved, the probe is moved back to the denatured area, or to a new location and the process is repeated. After the procedure is completed an eye patch is applied to the eye, or protective glasses worn, for approximately 12 hours.

Figure 6:
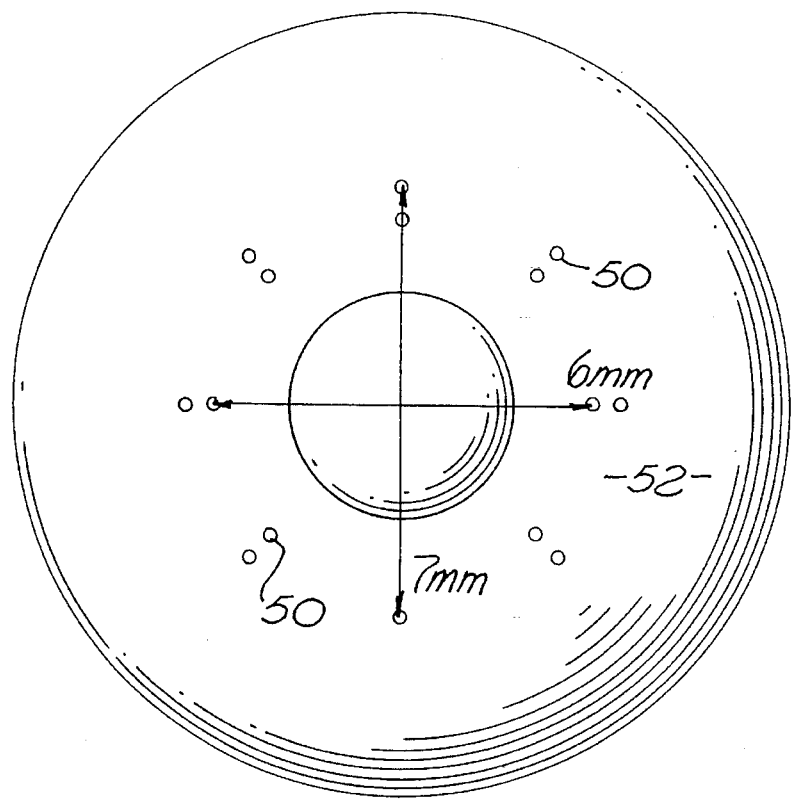
FIG. 6 is a top view showing a pattern of denatured areas of the cornea.

FIG. 6 shows a pattern of denatured areas 50 that have been found to correct hyperopic conditions. A circle of 8 denatured areas 50 are created about the center of the cornea, outside the visual axis portion 52 of the eye, with a nominal diameter of approximately 5 millimeters. The circle of denatured areas typically have a diameter of approximately 7 mm. If the first circle does not correct the eye deficiency, the same pattern may be repeated, or another pattern of 8 denatured areas may be created within a circle having a diameter of approximately 6 mm. It has been found that overcorrected hyperopic conditions may be reversed up to 80% by applying a topical cocaine to the denatured areas within 2 weeks of the procedure. The procedure of the present invention can then be repeated after a 30 day waiting period.

The exact diameter of the pattern may vary from patient to patient, it being understood that the denatured spots should preferably be formed in the non-visionary portion 52 of the eye. Although a circular pattern is shown, it is to be understood that the denatured areas may be located in any location and in any pattern. In addition to correcting for hyperopia, the present invention may be used to correct astigmatic conditions. The present invention may also be used to correct radial kerectotomy procedures that have overcorrected for a myopic condition.. The probe and power settings have been found to create denatured areas that do not reach the Decemets membrane. It had been found that denatured areas of the Decemets membrane in the field of vision may disturb the patients field of vision, particularly at night. The present invention leaves a scar that is almost imperceptible by slit lamp examination 6 months after the procedure.

Figure 7:
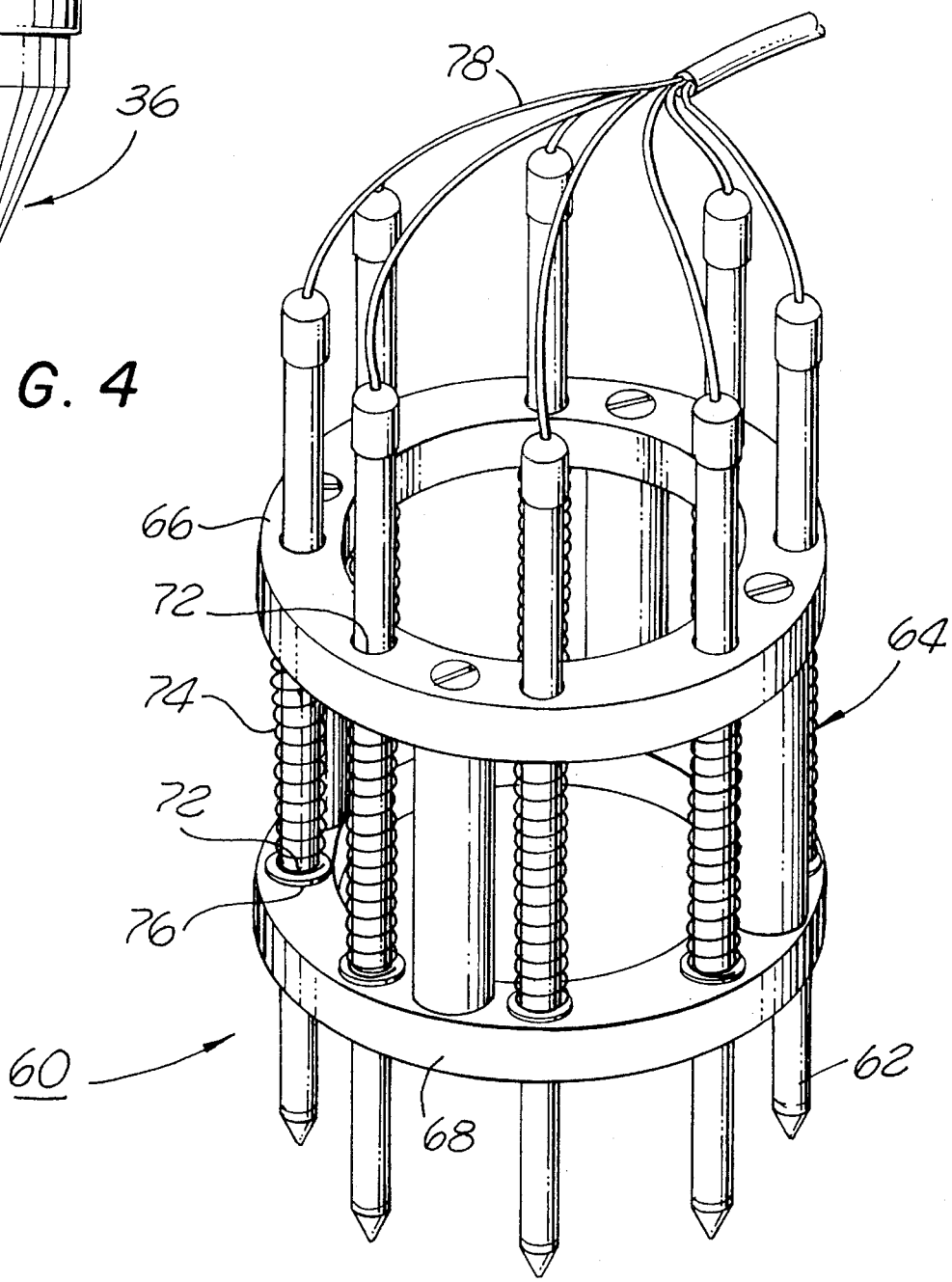
FIG. 7 is a perspective view of an alternate embodiment of the probe.

FIG. 7 shows an alternate embodiment of a probe 60 which has a plurality of first electrodes 62 coupled to a cage 64. The cage 64 includes a first ring 66 separated from a second ring 68 by a number of spacers 70. The cage 64 can be connected to a handle (not shown) which allows the surgeon to more easily utilize the probe 60.

The first electrodes 62 extend through apertures 72 in the rings 66 and 68. The electrodes 62 can move relative to the cage 64 in the directions indicated by the arrows. The probe 60 has a plurality springs 74 located between the rings and seated on washers 76 mounted to the electrodes 62. The springs 74 bias the electrodes 62 into the positions shown in FIG. 7. In the preferred embodiment, the probe 60 includes 8 electrodes arranged in a circular pattern having a 7.0 millimeter diameter.

In operation, the probe 60 is pressed onto the cornea so that the electrodes 62 move relative to the cage 64. The spring constant of the springs 74 is relatively low so that there is a minimal counterforce on the tissue. A current is supplied to the electrodes 62 through wires 78 attached thereto. The probe 60 is preferably used as uni-polar device, wherein the current flows through the tissue and into a "ground" pad located on the patient.

For surgeons who prefer "two handed" procedures, the probe could be constructed as two pieces, one piece being the first electrode, and the other piece being the second electrode. Although the probe has been described and shown denaturing a cornea, it is to be understood that the probes and methods of the present invention can be used to denature other tissue to correct for wrinkles, incontinence, etc. For example, the probe could be used to shrink a sphincter to correct for incontinence.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for reshaping a cornea of a patient, comprising the steps of:
    a) electrically grounding the patient;
    b) placing an electrode in contact with the cornea; and,
    c) sending a current through said electrode and into the cornea so that a local area of the cornea is heated and denatured.

2. The method as recited in claim 1, further comprising the steps of repeating steps (a) and (b).

3. The method as recited in claim 2, wherein the local denatured areas are arranged in a circular pattern about the tissue.

4. The method as recited in claim 3, wherein said denatured areas are located in a non-visual axis of the cornea.

5. The method as recited in claim 1, wherein said electrode creates a denatured area approximately 1.0 millimeter in diameter.

\* \* \* \* \*

(12) EX PARTE REEXAMINATION CERTIFICATE (7784th)
United States Patent
Hood et al.

(10) Number: US 5,533,999 C1
(45) Certificate Issued: Oct. 5, 2010

(54) METHOD AND APPARATUS FOR MODIFICATIONS OF VISUAL ACUITY BY THERMAL MEANS

(75) Inventors: Larry Hood, Laguna Hills, CA (US); Antonio Mendez G., Mexicali (MX)

(73) Assignee: Refractec, Inc., Irvine, CA (US)

Reexamination Request:
No. 90/006,962, Mar. 12, 2004

Reexamination Certificate for:
Patent No.: 5,533,999
Issued: Jul. 9, 1996
Appl. No.: 08/523,591
Filed: Sep. 5, 1995

Related U.S. Application Data

(63) Continuation of application No. 08/111,296, filed on Aug. 23, 1993, now abandoned.

(51) Int. Cl.
*A61B 18/08* (2006.01)

(52) U.S. Cl. ............................................. 606/5
(58) Field of Classification Search ............... None
See application file for complete search history.

(56) References Cited

U.S. PATENT DOCUMENTS

| | | | |
|---|---|---|---|
| 3,699,967 A | 10/1972 | Anderson | |
| 3,595,239 A | 7/1973 | Petersen | |
| 3,963,030 A | 6/1976 | Newton | |
| 4,252,419 A | * 2/1981 | Padula et al. | 351/204 |
| 4,301,802 A | 11/1981 | Poler | |
| 4,347,842 A | 9/1982 | Beale | |
| 4,386,608 A | 6/1983 | Ehrlich | |
| 4,419,747 A | 12/1983 | Jordan | |
| 4,500,832 A | 2/1985 | Mickiewicz | |
| 4,590,934 A | 5/1986 | Malis et al. | |
| 4,593,691 A | 6/1986 | Lindstrom et al. | |
| 4,674,499 A | 6/1987 | Pao | |
| 4,739,759 A | 4/1988 | Rexroth et al. | |
| 4,805,616 A | 2/1989 | Pao | |
| 4,898,169 A | 2/1990 | Norman et al. | |
| 4,907,585 A | * 3/1990 | Schachar | 606/28 |
| 4,955,378 A | 9/1990 | Grasso | |
| 5,054,906 A | 10/1991 | Lyons, Jr. | |
| 5,174,304 A | 12/1992 | Latina et al. | |
| 5,188,125 A | 2/1993 | Kilmer et al. | |
| 5,190,517 A | 3/1993 | Zieve et al. | |
| 5,195,954 A | 3/1993 | Schnepp-Pesch et al. | |
| 5,261,906 A | 11/1993 | Pennino et al. | |
| 5,277,696 A | 1/1994 | Hagen | |
| 5,376,089 A | 12/1994 | Smith | |
| 5,413,574 A | 5/1995 | Fugo | |
| 5,437,657 A | 8/1995 | Epstein | |

FOREIGN PATENT DOCUMENTS

WO    WO9012618 A1 * 11/1990

OTHER PUBLICATIONS

Definition of "Diathermy", "High Frequency Current", "Refractive Keratoplasty" and "Bipolar Cautery"—Stedman's Medical Dictionary, 27th ed., copyright 2002–2006.*
Gray's Anatomy, "The Organs of Special Sense", pp. 825–832, 1974 ed.*
Neumann et al, "II. Encouraging Results From Early Laboratory and Human Trials", Refractive & Corneal Surgery, vol. 5, Jan./Feb. 1989, pp. 50–54.*
"Anatomy of the Eye", pp. 3, 6–8, 21–22, date unknown.*
Fugo, "Bipokertoplasty: using cautery to advantage", Surgery News, Feb. 1, 1993.*
"Review of Ocular Anatomy", Physiology of the Eye–An Introduction to the Vegetative Functions, 2 ed., pp. 1–25, date unknown.*

(Continued)

*Primary Examiner*—Jeffrey R. Jastrzab

(57) ABSTRACT

A thermokeratoplastic electrode which has a tip that is placed in direct contact with the epithelium layer of the cornea. The electrode is capable of creating very small localized denatured areas that shrink the corneal membrane to correct hyperopic and astigmatic conditions.

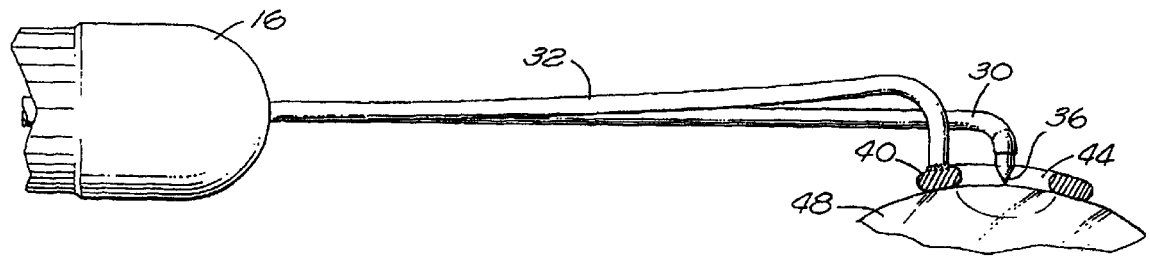

OTHER PUBLICATIONS

H. Treumer et al., "Unipolar Scleral Diathermy for Changing Corneal Refraction," Department for Ophthalmology, University Eye Clinic Kiel.

H. Treumer et al., "Temperature Controlled Bipolar Diathermy of the Sclera for Controlled Refractive Changes of the Cornea," Department of Ophthalmology University Eye Clinic Kiel, Fortschritte Ophthalmol (1989) 86: pp. 584–588.

Sebben, Jack E. "Cutaneous Electrosurgery", pp. 14–15, 19–30, 42–43, 48, 52–55, 62–62, 77–83, 100–105.

"Anatomy of the Eye", Physiology of the Eye, Chapter 1, pp. 3, 6–8, 21–22.

Mendez, Antonio "Radiofrequency for Hyperopia Treatment", Beverly Hills presentation, Aug. 28, 1993.

Voyles, Randel et al. "Biophysics of Electrosurgery", Excerpts from American College of Surgeons Meeting, San Francisco, CA, Oct. 1993.

McDonnell, Peter J. "Radial Thermokeratoplasty for Hyperopia". Refractive and Corneal Surgery, vol. 5, Jan./Feb. 1989, pp. 50–54.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-5 are cancelled.

* * * * *